(12) United States Patent
Ikeda et al.

(10) Patent No.: US 6,441,276 B1
(45) Date of Patent: Aug. 27, 2002

(54) ESR2 - A PLANT GENE THAT CAN PROMOTE SHOOT REGENERATION

(75) Inventors: Yoshihisa Ikeda; Nam-Hai Chua, both of New York City, NY (US)

(73) Assignee: The Rockefeller University, New York, NY (US)

(*) Notice: Subject to any disclaimer, the term of this patent is extended or adjusted under 35 U.S.C. 154(b) by 0 days.

(21) Appl. No.: 09/964,850

(22) Filed: Sep. 28, 2001

(51) Int. Cl.$^7$ .................. C12N 15/87; C12N 15/82; C12N 15/90; C12N 15/29
(52) U.S. Cl. .................. 800/290; 435/430; 435/468; 800/298
(58) Field of Search .................. 435/69.1, 320.1, 435/410, 419, 468, 430; 800/278, 290, 295, 298

(56) References Cited

PUBLICATIONS

Genbank accession No. AC000103*
Banno et al, "Overexpression of Arabidopsis ERS1 induces Initiation of Shoot Regeneration", Dec. 2001, The Plant Cell, vol. 13, pp. 2609–2618.*
Riechmann et al, "The AP2/EREBP Family of Plant Transaction Factors", 1998, Biol. Chem. vol. 379, pp. 633–646.*
Kizis et al, "Role of AP2/EREBP transcription factors in gene regulation during abiotic stress", 2001, FEBS Letters 498, pp. 187–189.*

* cited by examiner

*Primary Examiner*—Amy J. Nelson
*Assistant Examiner*—Ashwin D. Mehta
(74) *Attorney, Agent, or Firm*—Rothwell, Figg, Ernst & Manbeck (57) ABSTRACT

A plant gene, Esr2, has been found which when overexpressed in plant cells results in cells which have cytokinin-independent cell growth. This feature allows the encoded protein ESR2 to be used as a selectable marker of transformed cells by growing the transformed cells on cytokinin-free media. It has also been found that overexpression of ESR2 in cells grown in the presence of cytokinins results in a higher regeneration of plants. This feature allows the gene to be used to obtain greater regeneration of plant cells.

5 Claims, 4 Drawing Sheets

```
ATGGAAGAAGCAATCATGAGACTCGAAGGTGCCGAGCACAGAGAAACCAACATCCATTCT      60
 M  E  E  A  I  M  R  L  E  G  A  E  H  R  E  T  N  I  H  S      20

TTGAAAAGAAAGCCATCAAGAACTTCCTCGACAGCTCCTGGCTCTCCCGGAGGAGTAACT     120
 L  K  R  K  P  S  R  T  S  S  T  A  P  G  S  P  G  G  V  T      40

ACCGCAAAAGCTGCCTCCGGCGCCGGCGCTTCCGGTGTCTCTACGATAAGGTACCGAGGC     180
 T  A  K  A  A  S  G  A  G  A  S  G  V  S  T  I  R  Y  R  G      60

GTGAGGCGTAGGCCATGGGGTCGTTACGCAGCTGAAATACGGGACCCATTGTCCAAGGAG     240
 V  R  R  R  P  W  G  R  Y  A  A  E  I  R  D  P  L  S  K  E      80

AGACGATGGCTCGGAACATTTGACACGGCCGAGGAAGCAGCTTGCGCATATGACTGCGCC     300
 R  R  W  L  G  T  F  D  T  A  E  E  A  A  C  A  Y  D  C  A     100

GCTCGAGCCATGCGTGGTCTTAAAGCTCGAACCAACTTCGTCTACCCAATGCCTTCTCTC     360
 A  R  A  M  R  G  L  K  A  R  T  N  F  V  Y  P  M  P  S  L     120

GACTCTTATCACCACCGTATTTTCTCGTCTCCTCCAATGAATATGTTCCTTCTACGAGAC     420
 D  S  Y  H  H  R  I  F  S  S  P  P  M  N  M  F  L  L  R  D     140

GTGTTAAACTCTCAGTCTCTTTCTCCGTTAACCACTTTCGCTTACCCGCCTTGTAATCTT     480
 V  L  N  S  Q  S  L  S  P  L  T  T  F  A  Y  P  P  C  N  L     160

TCTAACGTAAACGACGTTGTTCACGAGTCCTTCACTAACGTCAACGATGTCTGTGAAGAT     540
 S  N  V  N  D  V  V  H  E  S  F  T  N  V  N  D  V  C  E  D     180

CTCTCGCCTAAAGCTAAGAGGTCAAGTACCATTGAGAACGAGAGCCTGATATCAAATATC     600
 L  S  P  K  A  K  R  S  S  T  I  E  N  E  S  L  I  S  N  I     200

TTTGAACCAGAACCAGCTAGTTCTGGTCTTCTTCAAGAAATTGTTCAAGGCTTCTTACCA     660
 F  E  P  E  P  A  S  S  G  L  L  Q  E  I  V  Q  G  F  L  P     220

AAACCTATCTCTCAACATGCTTCTATACCTCCAAAGAGCAACCAACAGTCGGTTGGTGTT     720
 K  P  I  S  Q  H  A  S  I  P  P  K  S  N  Q  Q  S  V  G  V     240

TTCCCGACGATGCCAGAGAGCGGTTTTCAGACAGATGTTCGTTTAGCTGACTTCCATGTC     780
 F  P  T  M  P  E  S  G  F  Q  T  D  V  R  L  A  D  F  H  V     260

GAAGGAAACGGATTCGGTCAGGTTAAATATCATGGAGAGTTAGGTTGGGCTGATCATGAG     840
 E  G  N  G  F  G  Q  V  K  Y  H  G  E  L  G  W  A  D  H  E     280

AATGGGTTTGATTCAGCTAAGATGCAGCAGAACGGAAATGGTGGAATGTTTTATCAGTAT     900
 N  G  F  D  S  A  K  M  Q  Q  N  G  N  G  G  M  F  Y  Q  Y     300

TGCTTTCATGATGATTATTAG                                            921
 C  F  H  D  D  Y  *                                             306
```

FIG. 1

```
ESR1  MEKALRNFTESTHSPDPNPLTKFFTEPTAHPVSRNRKLSSKDTIVTIAGA-GSSTIRYRG   59
ESR2  MEEAIMRLEGAFHRETNIHSLKRKPSRTSTTAPGSPGGVITAKAASGAGASGVSTIRYRG   60

ESR1  VRRRPWGRYAAEIRDPMSKERRWLGTFDTAEQAACAYDSAARAFRGAKARTNFTYPTAVI  119
ESR2  VRRRPWGRYAAEIRDPLSKERRWLGTFDTAEEAACAYDCAARAMRGLKARTNFVYPMPSL  120

ESR1  MPEPRFSFSNKKSSPSARCHLPSLPLDSSTQNFYGAPAAQRIMNTQSIFLRDASCSSRKT  179
ESR2  DSYHHRIFS----SP----PMNMFLLRDVLNSQSLSPLTTFAM--PPCNLSNVNDVVHES  170

ESR1  TPYNNSFNGSSSSYSASKTACVSYSENENNES-FFPEESSDTGLLQEVVQEFLKKNRGVP  239
ESR2  --FIN-VNDVCEDLSP-KAKRSSTIENESLISNLFEPEPASSGLLQEIVQGELPK----P  222

ESR1  PSPPTPPPVTSHHDNSGYESALTIYSENMVQETKETLSSKLDRYGNFQANDDGVRAVADG  298
ESR2  ISQHASTPPKSNQQSVGVFPTMP---ESGFQTDVRLADFHVEGNGFGQVKYHGELGWAD-  278

ESR1  GLSLGSNEWGYQEMLMYGTQLGCTCRRSWG                                328
ESR2  -HENGFDSAKMQONGNGGMFY-QYGFHDDY                                306
```

ESR2 - A PLANT GENE THAT CAN PROMOTE SHOOT REGENERATION

BACKGROUND OF THE INVENTION

Organogenesis in tissue culture is a critical step for efficient transformation of most plants. Media of controlled auxin/cytokinin ratio govern organogenesis in a wide range of species. Cytokinins were first identified as factors that act synergistically with auxin to promote cell division and act antagonistically to auxin to promote shoot and root initiation from callus cultures. Cytokinins have been implicated in many aspects of plant growth and development, including cell division, shoot initiation and growth, leaf senescence, and photomorphogenesis. Although most molecular mechanisms of cytokinin action are unknown, overexpression of a histidine kinase CKI1 or cyclin D3 confers cytokinin-independent cell growth on cultured cells of Arabidopsis (Kakimoto, 1996; Riou-Khamlichi et al., 1999), indicating that they may play key roles in cytokinin-signaling.

Transgenic techniques have become a powerful tool to address important biological problems in multicellular organisms, and this is particularly true in the plant field. Many approaches that were impossible to implement by traditional genetics can now be realized by transgenic techniques, including the introduction into plants of homologous or heterologous genes, with modified functions and altered expression patterns. The success of such techniques often depends upon the use of markers to identify the transgenic plants and promoters to control the expression of the transgenes.

Selectable markers are widely used in plant transformation. Historically such markers have often been dominant genes encoding either antibiotic or herbicide resistance (Yoder and Goldsbrough, 1994). Although such markers are highly useful, they do have some drawbacks. The antibiotics and herbicides used to select for the transformed cells generally have negative effects on proliferation and differentiation and may retard differentiation of adventitious shoots during the transformation process (Ebinuma et al., 1997). Also, some plant species are insensitive to or tolerant of these selective agents, and therefore, it is difficult to separate the transformed and untransformed cells or tissues (Ebinuma et al., 1997). Further, these genes are constitutively expressed, and there are environmental and health concerns over inserting such constitutively expressed genes into plants which are grown outside of a laboratory setting (Bryant and Leather, 1992; Gressel, 1992; Flavell et al., 1992).

One marker which is neither an antibiotic nor a herbicide is the ipt gene. This gene encodes isopentenyltransferase which is used in cytokinin synthesis (Barry et al., 1984). Overproduction of cytokinins results in the overproduction of shoots (Barry et al., 1984). This overproduction of shoots can result in a phenotype having a large number of shoots (hereafter "shooty phenotype"). This phenotype can be used as a marker (Ebinuma et al., 1997). A chimeric ipt gene under the control of the cauliflower mosaic virus (CaMV) promoter has been introduced into cells of potato (Ooms et al., 1983), cucumber (Smigocki and Owens, 1989), and several Nicotiana species (Smigocki and Owens, 1988) and these transgenic cells proliferated and exhibited an extreme shooty phenotype and loss of apical dominance in hormone-free medium. Studies have shown that in plants transformed with ipt to overproduce cytokinins, the cytokinins work only locally as a paracrine hormone (Faiss et al., 1997). One problem with the use of ipt as a marker is that the resulting transgenic plants lose apical dominance and are unable to root due to overproduction of cytokinins (Ebinuma et al., 1997).

Ebinuma et al. (1997) developed one method to use the ipt marker and to overcome the problems noted above. They developed a vector in which the ipt gene was inserted into a plasmid which included the transposable element Ac. The construct included the T-DNA (portion of the Ti plasmid that is transferred to plant cells) and the 35S CaMV promoter. This construct was transformed into *A. tumefaciens*. Leaf segments were inoculated with the transformed bacteria and grown on nonselective media. Abnormal shoots with an extra shooty phenotype were selected and cultivated further for six months. From these, several normal shoots grew. Some of these were a result of the transposable element Ac having excised from the genome along with the ipt gene. This was determined by DNA analysis. Some of these few plants retained the other necessary markers which had also been included in the plasmid. This method therefore overcomes the problems of having a constitutively expressed ipt gene present. Unfortunately, this method requires many months of cultivation and results in only a few plants which have lost the ipt gene. Ebinuma et al. (1997) report that 6 months after infection the frequency of marker free plants was 0.032%.

The gene CKI1 was more recently identified (Kakimoto, 1996). Overproduction of this gene in plants results in plants which exhibit typical cytokinin responses, including rapid cell division and shoot formation in tissue culture in the absence of exogenous cytokinin (Kakimoto, 1996). The CKI1 gene can be used as a selectable marker in a manner similar to ipt, i.e., the CKI1 gene can be put under the control of a promoter and overexpressed in transgenic plant cells thereby inducing shoot formation in the absence of exogenous plant hormones. Such shoots can be excised thereby obtaining transgenic plants. Such shoots, obtained either from cells transformed with ipt or CKI, cannot be made to grow normally while the cells are expressing these transgenes. The knotted gene and knotted-like genes are a third group of genes which when overexpressed can lead to ectopic production of adventitious shoots (Chuck et al., 1996; Lincoln et al., 1994). These can be used as selectable markers in the same manner as the ipt and CKI1 genes.

Besides the use of markers to identify transgenic plants, the use of promoters to control the transgenes is a normal part of such experiments. In most experiments, the transgenes are transcribed from a strong promoter, such as the 35S promoter of the cauliflower mosaic virus (CaMV). However, a more flexible gene expression system is needed to extract greater benefits from transgenic technology. Good inducible transcription systems are desired because transgenic plants with inducible phenotypes are as useful as conditional mutants isolated by traditional genetics. In this regard, several induction systems have been reported and successfully used (Ainley and Key, 1990; Gatz et al., 1992; Mett et al., 1993; Weinmann et al., 1994). Among these, the tetracycline-dependent expression systems are the most commonly used (for review, see Gatz, 1996). See Zuo and Chua (2000) for a review of chemical-inducible systems for regulated expression of plant genes.

The glucocorticoid receptor (GR) is a member of the family of vertebrate steroid hormone receptors. GR is not only a receptor molecule but also a transcription factor which, in the presence of a glucocorticoid, activates transcription from promoters containing glucocorticoid response elements (GREs) (for reviews, see Beato, 1989; Picard, 1993). It had been considered that the GR system could be a good induction system in plants because it is simple, and glucocorticoid itself does not cause any pleiotropic effects in plants. Schena et al. (1991) demonstrated that a system comprising GR and GREs could work in a transient expression system with cultured plant cells. It had been reported that the hormone-binding domain (HBD) of GR could regulate the function of plant transcription factors in transgenic plants (Aoyama et al., 1995; Lloyd et al., 1994). Aoyama and Chua (1997) then demonstrated a general and efficient glucocorticoid-inducible system using GR.

Despite the availability of the markers described above and the systems available for controlling the expression of the markers, the need for improved marker genes still exists. Furthermore, a need exists for improving the efficiency of organogenesis or regeneration of plant cells. The present invention addresses both of these needs.

The publications and other materials used herein to illuminate the background of the invention, and in particular cases to provide additional details respecting the practice, are incorporated herein by reference, and for convenience, are referenced by author and date in the text and respectively grouped in the appended List of References.

SUMMARY OF THE INVENTION

One aspect of the invention is a method of using ESR2 as a selectable marker.

Overexpression of ESR2 in plants or plant cells results in plants or cells which show cytokinin-independent growth. This allows the gene to be used as a selective marker by growing cells transformed with the gene in cytokinin-free medium.

Another aspect of the invention is that overexpression of ESR2 in plant cells grown in the presence of cytokinins results in extremely high regeneration efficiency. This aspect of the invention uses the gene not as a marker but as a means to increase the regeneration efficiency of plant cells.

BRIEF DESCRIPTION OF THE FIGURES

FIG. 1 shows the nucleotide (SEQ ID NO:1) and amino acid (SEQ ID NO:2) sequences of ESR2. The EREBP/AP2 domain is underlined and the stop codon is shown by an asterisk.

DETAILED DESCRIPTION OF THE INVENTION

We have isolated and examined an Esr1 homolog, termed Esr2, the overexpression of which, similar to the overexpression of Esr1, confers cytokinin-independent shoot regeneration on Arabidopsis root explants, even though the entire sequence identity between Esr1 and Esr2 is only 40%. Shoot formation by either Esr1 or Esr2 overexpression in the absence of cytokinin may be due to an increased sensitivity to a low level of endogenous cytokinin which by itself is not sufficient to induce shoot formation in wild type root cultures. Data discussed below indicates that root explants overexpressing ESR2 are more sensitive than those overexpressing ESR1. We have previously shown that the optimum concentration of cytokinin in root explants overexpressing ESR1 was shifted to a lower value (Banno et al., 2001) as compared to explants with a normal expression of ESR1. Taking this result into consideration, it is possible that the optimum concentration of cytokinin in root explants overexpressing ESR2 is shifted to an even lower value than for root explants overexpressing ESR1. We conclude that the ESR2 gene can be used to promote shoot regeneration in transformation experiments.

The present invention relates to transgenic plants which include the gene Esr2 (enhancer of shoot regeneration 2). This gene is shown as SEQ ID NO:1 and is a distant homolog of Esr1 which is shown as SEQ ID NO:3. The respective proteins encoded by these genes, ESR2 and ESR1, are shown as SEQ ID NOs:2 and 4, respectively. Esr1 is nearly identical with a gene reported in GenBank (Accession Number AC007357, gene F3F19.1 consisting of bases 2481–3467 of the GenBank sequence which is shown herein as SEQ ID NO:5 and its encoded protein as SEQ ID NO:6). The GenBank sequence differs from the Esr1 gene at four bases and the encoded proteins differ at a single amino acid residue. ESR2 performs functions similar to ESR1, but the activity of ESR2 is greater than that of ESR1. Overexpression of Esr2 allows cytokinin-independent growth of the plants or cells which are overexpressing the gene thereby allowing the gene to be used as a marker. Furthermore, overexpression of the gene in cells grown in the presence of cytokinins results in a high regeneration efficiency, thus allowing the gene to be used in a manner which increases plant regeneration.

Expression of Esr2 can be placed under the control of an inducible promoter. An inducible promoter can be one which can be turned on (induced) to select for cells or plants which have become transgenic but which will not be turned on under natural growth conditions. In this manner the selectable marker gene, although present in the transgenic plants, will be completely silent during the normal growth of the plants and should not interfere with the growth of the plants. Such a silent marker gene may also be more environmentally acceptable than, e.g., having an antibiotic resistance gene marker present wherein said resistance gene is expressed during the normal growth of the plant.

To use ESR2 as a silent marker, Esr2 can be placed in a vector with an inducible promoter and plant cells are then transformed with the vector. The plant cells are grown in the presence of an inducer to turn on expression of ESR2 but in media lacking cytokinins. The absence of cytokinins prevents the growth of nontransformed cells, but cells transformed with the vector will grow despite the lack of cytokinins in the medium because of overexpression of the ESR2 gene. Shoots or calli which grow can be selected and tested to ascertain that they do include the vector. Once transformed shoots or calli are selected, they can be grown under normal conditions in the absence of inducer thereby preventing expression of the ESR2 gene within the vector.

The vector which expresses Esr2 under the control of an inducible promoter can, if desired, include a second gene which will be expressed. This second gene can be under the control of an inducible promoter which is different from that controlling the ESR2 gene or it can be under the control of a constitutive promoter. This second gene can then be induced or produced constitutively in the transformed plants which are grown under normal conditions. The second gene can be any gene desired and can produce a protein which results in a more desirable trait than found in the nontransformed plant. Alternatively, plants can be cotransformed with one vector encoding ESR2 and with a second vector encoding the gene of interest. As the two transgenes will segregate in subsequent transgenic generations, transgenic plants carrying only the gene of interest can be obtained this way.

One inducible promoter under which the Esr2 gene can be placed is the glucocorticoid receptor (Aoyama and Chua, 1997). This has been considered to be a good induction system for plants because glucocorticoid itself does not cause any apparent pleiotropic effects in plants. The use of a steroid receptor domain to regulate gene expression in transgenic plants has been previously reported by Lloyd et al. (1994), who showed that trichome development in Arabidopsis could be successfully controlled by a chimeric protein comprising the glucocorticoid receptor domain and the maize transcriptional regulator R. Tight transcriptional regulation with these systems appears to be dependent on the intramolecular structure of the chimeric protein, especially the relative position between the glucocorticoid receptor domain and the domain whose function is to be regulated. Although the glucocorticoid receptor-regulated promoter is a useful one which can be used together with ESR2, Esr2 can be used together with any inducible promoter which is desired. For a recent review of chemical-inducible systems for regulated expression of plant genes see Zuo and Chua (2000).

In addition to its use as a marker, especially as a silent marker, overexpression of Esr2 in the presence of cytokinins results in enhanced regeneration efficiency. This result allows one several options for increasing yields of transformed plants. Vectors can be prepared which contain both a gene of interest as well as Esr2. Plant cells are then transformed with these vectors and the cells are cultured. In a first method, the cells can first be cultured on media lacking cytokinins but including an inducer of the ESR2 gene and the shoots and calli which grow can be selected and then grown normally. In a second method, the cells can be grown on media with cytokinins and with an inducer of Esr2. This second method allows greater regeneration efficiency thereby resulting in more shoot or callus formation. If desired, this second method can be performed with a vector comprising yet a third gene which can encode a selectable marker, e.g., an antibiotic resistance gene. In this method, a vector comprising Esr2 under the control of an inducible promoter, the antibiotic resistance marker gene, and the gene of interest is used to transform cells. The cells are then grown on a medium with an inducer of Esr2, an antibiotic, and cytokinins. The expression of Esr2 results in enhanced regeneration efficiency while the antibiotic resistance gene acts as a selectable marker. The gene of interest will be present in the selected shoots.

The vectors to be used in forming transgenic plants can include a chemically inducible promoter such as the glucocorticoid promoter which will activate the selectable marker but can include any other desired promoter in place of or in addition to the GR system promoter. If desired, any other gene of interest can also be put under control of the inducible promoter such that the gene could be turned on whenever desired. Such a gene need not be a marker.

The present invention is described by reference to the following Examples, which are offered by way of illustration and are not intended to limit the invention in any manner. Standard techniques well known in the art or the techniques specifically described below were utilized.

EXAMPLE 1

Cloning and Construction of ESR Clones

ESR1 was isolated and cloned as described previously (Banno et al., 2001). Based on the sequence similarity to ESR1, the ESR2 gene was identified as the most homologous gene in the Arabidopsis thaliana genome. The coding region of ESR2 was amplified from the Arabidopsis genomic DNA (Columbia ecotype) by PCR using primers for FWD: 5'-TAGGCGCGCCATGGAAGAAG-3' (SEQ ID NO:7) and for RV: 3'-GCGGCCGCATTTCTTTACAAC-5' (SEQ ID NO:8). Amplified fragments were ligated into pPCR-Script Amp vector (STRATAGENE), resulting in pPCR-ESR2 and the sequence was confirmed. The resulting construct, pPCR-ESR2, was digested with AscI and NotI and the digested fragments were cloned between a cauliflower mosaic virus 35S promoter and the poly A addition sequence of the nopaline synthetase gene in the plasmid pSK34, a derivative of pSK1, resulting in pSK-ESR2 (Kojima et al., 1999). pPCR-ESR2 was also digested with AscI and SpeI and cloned into pER10 digested with AscI and SpeI, resulting inpER10-ESR2. pER10-ESR1 was constructed by ligating the AscI-NotI fragment of the ESR1 cDNA to linearized pER10. pER10 is identical to pER8 (Zuo et al., 2000), except that the hygromycin-resistance gene is replaced by a kanamycin-resistance gene. The plasmid constructs were transformed into root cultures mediated by *Agrobacterium tumefaciens* EHA105. Root transformation was carried out as described previously (Koncz et al., 1989).

EXAMPLE 2

Plant Materials and Growth Conditions

*Arabidopsis thaliana* Wassilewskija (WS) was used for root cultures. Seeds were sterilized and sown on MS medium [Murashige and Skoog (MS) salts (Sigma), Gamborg's B5 vitamins (Sigma), 1% sucrose and 0.25% Phytagel (Sigma)] and grown for 7 days at 22° C. under continuous light. Seedlings were transferred to B5 liquid medium [Gamborg's B5 salts (Sigma), Gamborg's B5 vitamins and 2% glucose] and incubated for 15 days with shaking at 125 rpm. Aerial parts were removed from the hydroponic culture and the harvested roots were cultured. Cultured roots were cut into 3–6 mm segments and used for transformation. Compositions of the callus-inducing medium (CI medium), the shoot-regeneration medium (SR medium) and the root-inducing medium (RI medium) were as follows (Yasutani et al., 1994): (1) CIM: Gamborg's B5 salts, 2% glucose, Gamborg's B5 vitamins, 2 $\mu$M 2,4-dichloroacetic acid (2,4-D), 0.25 $\mu$M kinetin, 50 mg/L of kanamycin, 0.1 g/L of carbenicillin, and 0.25% Phytagar; (2) SRM: MS salts, 1% sucrose, Gamborg's B5 vitamins, 0.8 $\mu$M indole-3-acetic acid (IAA), 12.5 $\mu$M $N^6$-$\delta^2$-isopentenyladenine (2-ip), 50 mg/L of kanamycin, 0.1 g/L of carbenicillin and 0.25%

Phytagar; (3) RIM: Gamborg's B5 salts, 2% glucose, Gamborg's B5 vitamins, 2.5 μM IAA, 50 mg/L of kanamycin, 0.1 g/L of carbenicillin and 0.25% Phytagar. The constructs were introduced into Arabidopsis roots by Agrobacterium-mediated transformation and the roots were incubated on plates with or without cytokinin and in the presence or absence of the inducer. 17-β-estradiol was purchased from Sigma (St. Louis, Mo, USA) and treated as an inducer to become 10 μM as a final concentration.

EXAMPLE 3

Sequence Analysis of Two ESR Genes

Figure 2:
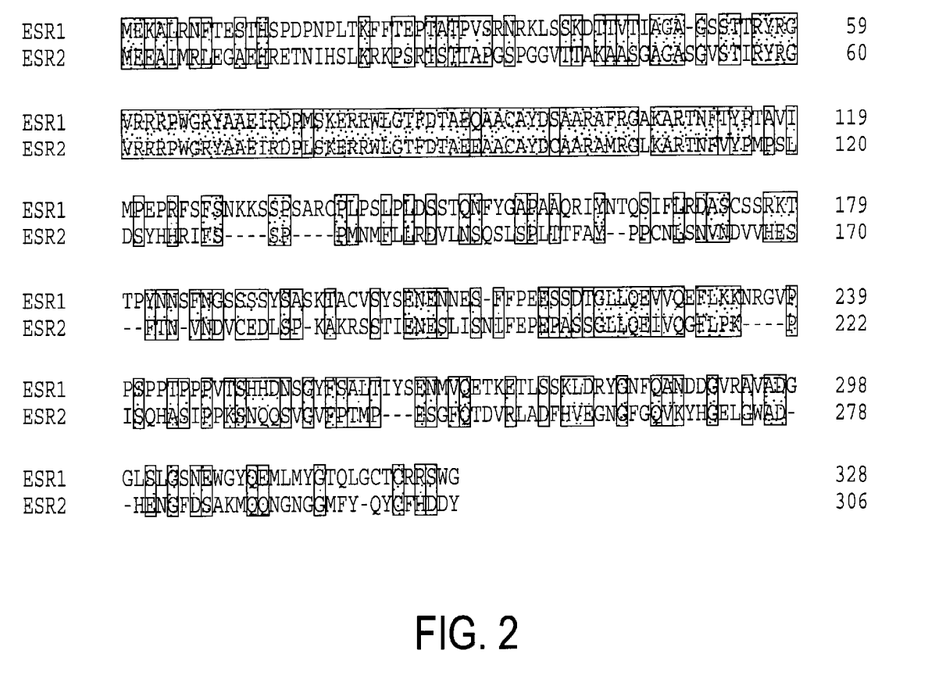
FIG. 2 is a comparison of the amino acid sequences of ESR1 (SEQ ID NO:4) and ESR2 (SEQ ID NO:2). Gaps denoted by dashes were inserted to achieve maximum homology. Identical amino acid residues between the two sequences are indicated by white letters on a black background and similar amino acid residues between the two sequences are black letters with shading.

Sequence analysis predicted that ESR1 encodes a protein of 328 amino acids with a molecular mass of 36.27 kDa. ESR2 encodes a protein of 306 amino acids with a molecular mass of 33.83 kDa (FIG. 1). Both proteins contain a domain with sequence homology to the AP2/ERBP domain found in a group of transcriptional factors in higher plants (Chang and Shockey, 1999; Okamuro et al., 1997; Riechmann and Meyerowitz, 1998). ESR2 was isolated as an ESR1 homolog from the database search, however, the entire amino acid identity is no more than 40%. Whereas the AP2/EREBP domain of both ESR proteins is highly conserved, the proteins have little sequence similarity to each other beyond the AP2/EREBP domain (FIG. 2). Genomic genes corresponding to each cDNA are found in GenBank and are assigned to chromosome 1 (GenBank AC007357 (similar to Esr1) and GenBank AC000103 (for Esr2)).

EXAMPLE 4

Effects of Constitutive Expression of Two ESR Genes on Plants

Figure 3:
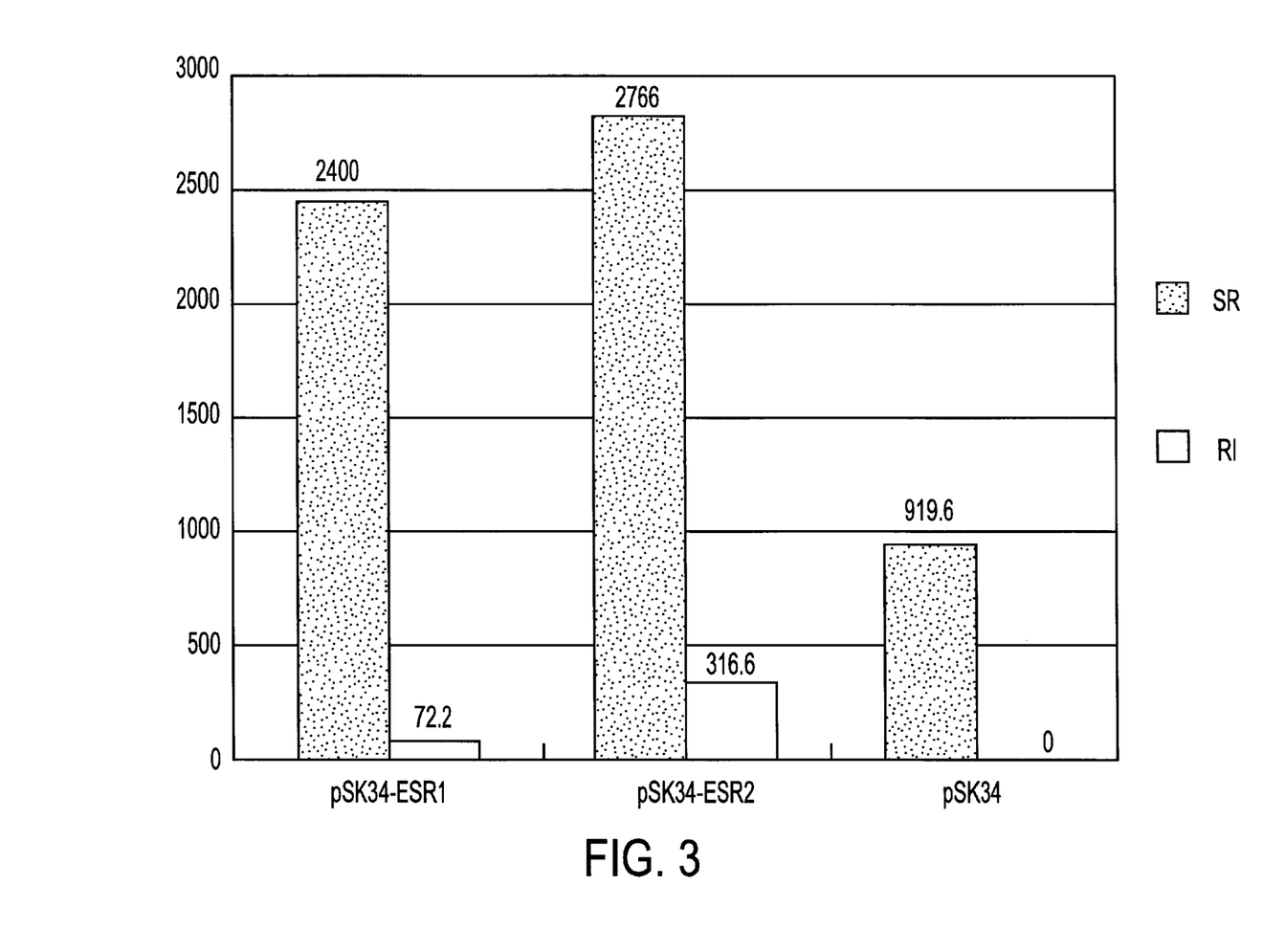
FIG. 3 shows the effects of constitutive overexpression of ESR1 or ESR2 on transformation. The number of transformed green calli obtained from 1 g fresh weight of root culture was calculated 4 weeks after transformation and are shown on the left. The open columns show the number of green calli grown on RI medium and the filled columns show the number of green calli grown on SR medium.

Root explants were transformed either with a CaMV 35S-ESR1 or CaMV 35S-ESR2 construct and the number of transformed calli grown on SR medium or RI medium was calculated. Whereas the transformed calli harboring empty vector grew only in the SR medium, the transformed calli harboring one of the Esr containing constructs grew on SR medium and on RI medium and showed the same morphology as the empty vector calli. These calli harboring one of the Esr containing constructs are darker green than those of the empty vector and unable to produce any shoots. By contrast, approximately 80% of calli carrying the empty-vector developed into transgenic plants. In the presence of cytokinin (12.5 μM 2-ip; SR medium), overexpression of either the ESR1 or ESR2 gene also significantly increased the number of green calli (2.6- and 3-fold, respectively). In the absence of cytokinin, the number of green calli transformed either with CaMV 35S-ESR1 or CaMV 35S-ESR2 resulted in 72.2 and 316.6 calli per 1.0 gram fresh weight root explants, respectively (FIG. 3).

EXAMPLE 5

Effects of Transient Expression of Two ESR Genes by XVE System

Figure 4:
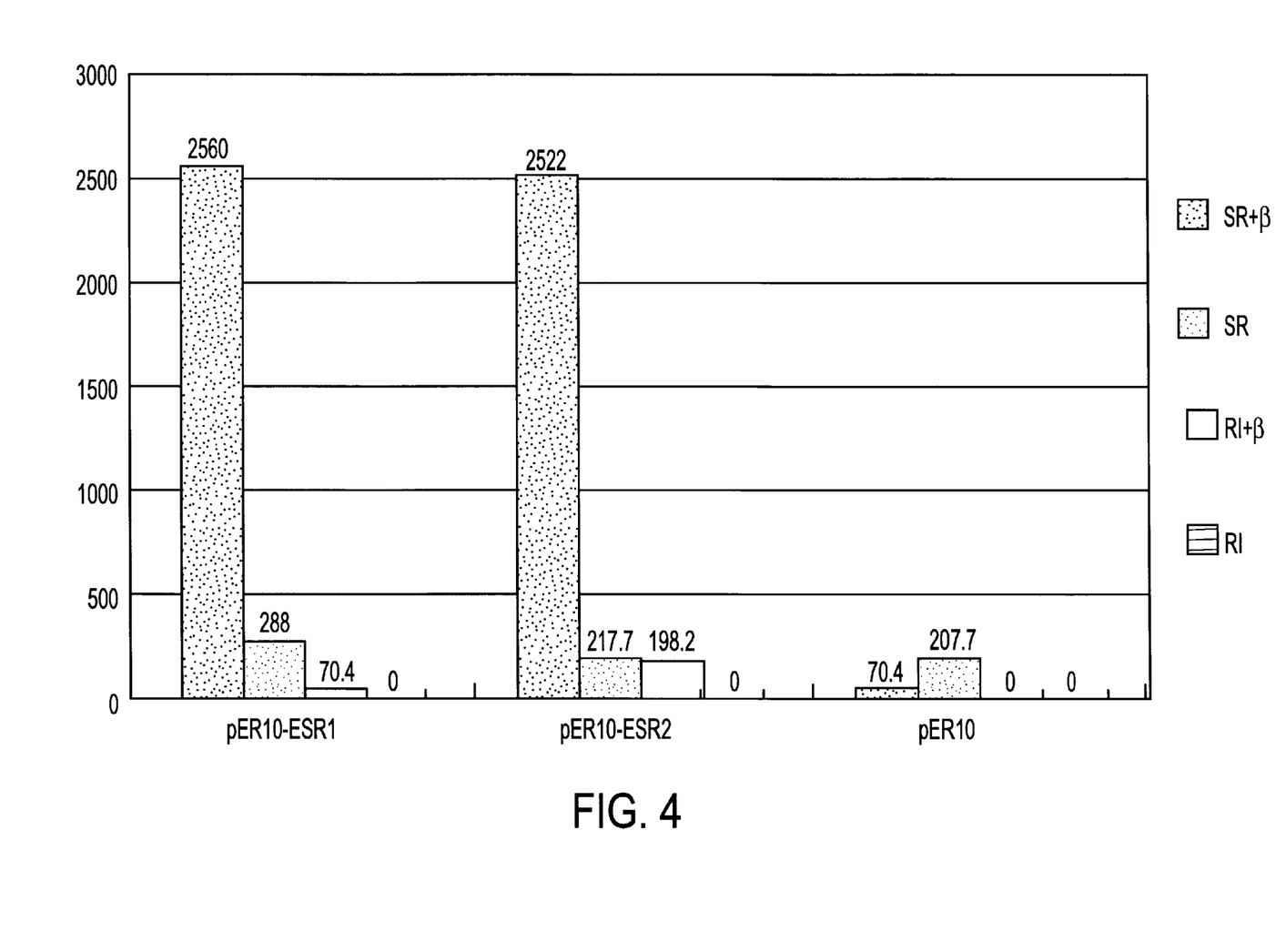
FIG. 4 shows the effects of inducible expression of ESR1 or ESR2 on shoot regeneration. The number of shoots obtained from 1 g fresh weight of root culture was calculated 4 weeks after transformation and is shown on the left. Arabidopsis root cultures transformed with the vector alone (pER10) or with each of the two ESR genes were cultured on SR medium with (black filled columns) or without (gray filled columns) an inducer (10 μM 17-β-estradiol) or were cultured on RI medium with (open columns) or without (hatched columns) the 17-β-estradiol (10 μM) inducer.

The effect of shoot regeneration under the control of the estradiol-inducible XVE system was examined. Root explants were transformed either with a pER10-ESR1 or pER10-ESR2 construct and the number of regenerated shoots grown on SR or RI medium either with or without inducer was determined. Whereas constitutive expression of either of the ESR genes inhibited shoot regeneration and resulted in darker green calli, transient overexpression of them by the XVE system regenerated shoots in a 17-β-estradiol dependent manner. In the absence of cytokinin, shoots were regenerated either from the root explants induced to overexpress ESR1 or ESR2. In this condition, shoot regeneration efficiency induced by ESR2 is 2.8 times higher than that by ESR1. In the presence of cytokinin, shoot regeneration efficiency induced by ESR2 is almost the same as that by ESR1 (FIG. 4).

While the invention has been disclosed herein by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

References

Ainley W M and Key J L (1990). *Plant Mol. Biol.* 14:949–966.

Aoyama T and Chua N-H (1997). *The Plant J.* 11:605–612.

Aoyama T, Dong C-H, Wu Y, Carabelli M, Sessa G, Ruberti I, Morelli G and Chua N-H (1995). *Plant Cell* 7:1773–1785.

Banno H, Ikeda Y, Niu Q W and Chua N H (2001). "Overexpression of Arabidopsis ESR1 induces initiation of shoot regeneration." Plant Cell (in press).

Barry G F, Rogers S G, Fraley R T and Brand L (1984). *Proc. Natl. Acad. Sci. USA* 81:4776–4780.

Beato M (1989). *Cell* 56:335–344.

Bryant J and Leather S (1992). *Trends Biotechnol.* 10:274–275.

Chang C and Shockey J A (1999). *Curr. Opin. Plant Biol.* 2:352–358.

Chuck G, Lincoln C and Hake S (1996). *The Plant Cell* 8:1277–1289.

Ebinuma H, Sugita K, Matsunaga E and Yamakado M (1997). *Proc. Natl. Acad. Sci. USA* 94:2117–2121.

Faiss M, ZalubìlováJ, Strnad M and Schmülling T (1997). *The Plant Journal* 12:401–415.

Flavell R B, Dart E, Fuchs R L and Fraley R B (1992). *Bio/Technology* 10:141–144.

Gatz C (1996). *Curr. Opin. Biotechnol.* 7:168–172.

Gatz C, Frohberg C and Wendenburg R (1992). *Plant J.* 2:397–404.

Gressel J (1992). *Trends Biotechnol.* 10:382.

Kakimoto T (1996). *Science* 274:982–985.

Kojima S, Banno H, Yoshioka Y, Oka A, Machida C and Machida Y (1999). *DNA Res.* 6:407–410.

Koncz C, Martini N, Mayerhofer R, Koncz-Kalman Z, Korber H, Redei G P and Schell J (1989). *Proc. Natl. Acad Sci. USA* 86:8467–8471.

Lincoln C, Long J, Yamaguchi J, Serikawa K and Hake S (1994). *The Plant Cell* 6:1859–1876.

Lloyd A M, Schena M, Walbot V and Davis R W (1994). *Science* 266:436–439.

Mett V L, Lockhead L P and Reynolds P H S (1993). *Proc. Natl. Acad. Sci. USA* 90:4567–4571.

Okamuro J K, Caster B, Villarroel R, Van Montagu M and Jofuku K D (1997). *Proc. Natl. Acad. Sci. USA* 94:7076–7081.

Ooms G, Kaup A and Roberts J (1983). *Theor. Appl. Genet.* 66:169–172.

Picard D (1993). *Trends Cell Biol.* 3:278–280.

Riechmann J L and Meyerowitz E M (1998). *Biol. Chem.* 379:633–646.

Riou-Khamlichi C, Huntley R, Jacqmard A and Murray J A (1999). *Science* 283:1541–1544.

Schena M, Lloyd A M and Davis R W (1991). *Proc. Natl. Acad. Sci. USA* 88:10421–10425.

Smigocki A C and Owens L D (1988). *Proc. Natl. Acad. Sci. USA* 85:5131–5135.

Smigocki A C and Owens L D (1989). *Plant Physiol.* 91:808–811.

Weinmann,P, Gossen M, Hillen W, Bujard H and Gatz C (1994). *Plant J.* 5:559–569.

Yasutani I, Ozawa S, Nishida T, Sugiyarna M and Komamine A (1994). *Plant Physiol.* 105:815–822.

Yoder J I and Goldsbrough A P (1994). *Bio/Technology* 12:263–267.

Zuo J and Chua N-H (2000). *Current Opinion in Biotechnology* 11:146–151.

Zuo J, Niu Q W and Chua N H (2000). *Plant J.* 24:265–273.

What is claimed is:

1. A method of selecting a transgenic plant comprising:
(a) transforming plant cells with a vector comprising a nucleotide sequence encoding the protein of SEQ ID NO: 2, wherein said nucleotide sequence is under the control of an inducible promoter;
(b) culturing said plant cells in media comprising an inducer of said inducible promoter to produce plants under conditions wherein said protein is expressed; and
(c) selecting the plants which are produced in step (b); wherein said media in step (b) lacks the concentration of cytokinin necessary to support regeneration of shoots from plant cells that do not comprise said nucleotide sequence, and wherein said plants selected in step (c) are plants which are transgenic.

2. The method of claim 1 wherein said vector further comprises a gene of interest.

3. A method for increasing regeneration efficiency of transformed plant cells comprising:

(a) transforming plant cells with a vector comprising a nucleotide sequence encoding the protein of SEQ ID NO: 2;

(b) growing said plant cells in media comprising cytokinin to produce shoots under conditions wherein said protein is expressed; and (c) growing said shoots to produce plants;

wherein said nucleotide sequence is under the control of an inducible promoter and step (b) is performed in the presence of an inducer of said inducible promoter, and wherein regeneration of shoots from said plant cells produced in step (b) occurs at a higher rate than does regeneration of shoots from plant cells that do not comprise said nucleotide sequence.

4. The method of claim 3 wherein said vector further comprises a gene of interest.

5. A method for increasing regeneration efficiency of transformed plant cells comprising:

(a) transforming plant cells with a vector comprising a gene of interest wherein said plant cells were previously transformed with a first vector comprising a nucleotide sequence encoding the protein of SEQ ID NO: 2;

(b) culturing the plant cells produced in step (a) in media comprising cytokinin to produce shoots under conditions wherein said protein is expressed; and (c) growing said shoots to produce plants;

wherein said nucleotide sequence is under the control of an inducible promoter and step (b) is performed in the presence of an inducer of said inducible promoter and wherein regeneration of shoots produced in step (b) occurs at a higher rate than does regeneration of shoots from plant cells that do not comprise said nucleotide sequence.

* * * * *

SEQUENCE LISTING

```
<160> NUMBER OF SEQ ID NOS: 8

<210> SEQ ID NO 1
<211> LENGTH: 921
<212> TYPE: DNA
<213> ORGANISM: Arabidopsis thaliana
<220> FEATURE:
<221> NAME/KEY: CDS
<222> LOCATION: (1)..(918)

<400> SEQUENCE: 1 atg gaa gaa gca atc atg aga ctc gaa ggt gcc gag cac aga gaa acc      48
Met Glu Glu Ala Ile Met Arg Leu Glu Gly Ala Glu His Arg Glu Thr
1               5                  10                  15 aac atc cat tct ttg aaa aga aag cca tca aga act tcc tcg aca gct      96
Asn Ile His Ser Leu Lys Arg Lys Pro Ser Arg Thr Ser Ser Thr Ala
            20                  25                  30 cct ggc tct ccc gga gga gta act acc gca aaa gct gcc tcc ggc gcc     144
Pro Gly Ser Pro Gly Gly Val Thr Thr Ala Lys Ala Ala Ser Gly Ala
        35                  40                  45 ggc gct tcc ggt gtc tct acg ata agg tac cga ggc gtg agg cgt agg     192
Gly Ala Ser Gly Val Ser Thr Ile Arg Tyr Arg Gly Val Arg Arg Arg
    50                  55                  60 cca tgg ggt cgt tac gca gct gaa ata cgg gac cca ttg tcc aag gag     240
Pro Trp Gly Arg Tyr Ala Ala Glu Ile Arg Asp Pro Leu Ser Lys Glu
65                  70                  75                  80 aga cga tgg ctc gga aca ttt gac acg gcc gag gaa gca gct tgc gca     288
Arg Arg Trp Leu Gly Thr Phe Asp Thr Ala Glu Glu Ala Ala Cys Ala
                85                  90                  95 tat gac tgc gcc gct cga gcc atg cgt ggt ctt aaa gct cga acc aac     336
Tyr Asp Cys Ala Ala Arg Ala Met Arg Gly Leu Lys Ala Arg Thr Asn
            100                 105                 110 ttc gtc tac cca atg cct tct ctc gac tct tat cac cac cgt att ttc     384
Phe Val Tyr Pro Met Pro Ser Leu Asp Ser Tyr His His Arg Ile Phe
        115                 120                 125 tcg tct cct cca atg aat atg ttc ctt cta cga gac gtg tta aac tct     432
Ser Ser Pro Pro Met Asn Met Phe Leu Leu Arg Asp Val Leu Asn Ser
    130                 135                 140 cag tct ctt tct ccg tta acc act ttc gct tac ccg cct tgt aat ctt     480
Gln Ser Leu Ser Pro Leu Thr Thr Phe Ala Tyr Pro Pro Cys Asn Leu
145                 150                 155                 160 tct aac gta aac gac gtt gtt cac gag tcc ttc act aac gtc aac gat     528
Ser Asn Val Asn Asp Val Val His Glu Ser Phe Thr Asn Val Asn Asp
                165                 170                 175 gtc tgt gaa gat ctc tcg cct aaa gct aag agg tca agt acc att gag     576
Val Cys Glu Asp Leu Ser Pro Lys Ala Lys Arg Ser Ser Thr Ile Glu
            180                 185                 190
```

```
aac gag agc ctg ata tca aat atc ttt gaa cca gaa cca gct agt tct     624
Asn Glu Ser Leu Ile Ser Asn Ile Phe Glu Pro Glu Pro Ala Ser Ser
            195                 200                 205 ggt ctt ctt caa gaa att gtt caa ggc ttc tta cca aaa cct atc tct     672
Gly Leu Leu Gln Glu Ile Val Gln Gly Phe Leu Pro Lys Pro Ile Ser
    210                 215                 220 caa cat gct tct ata cct cca aag agc aac caa cag tcg gtt ggt gtt     720
Gln His Ala Ser Ile Pro Pro Lys Ser Asn Gln Gln Ser Val Gly Val
225                 230                 235                 240 ttc ccg acg atg cca gag agc ggt ttt cag aca gat gtt cgt tta gct     768
Phe Pro Thr Met Pro Glu Ser Gly Phe Gln Thr Asp Val Arg Leu Ala
                245                 250                 255 gac ttc cat gtc gaa gga aac gga ttc ggt cag gtt aaa tat cat gga     816
Asp Phe His Val Glu Gly Asn Gly Phe Gly Gln Val Lys Tyr His Gly
            260                 265                 270 gag tta ggt tgg gct gat cat gag aat ggg ttt gat tca gct aag atg     864
Glu Leu Gly Trp Ala Asp His Glu Asn Gly Phe Asp Ser Ala Lys Met
        275                 280                 285 cag cag aac gga aat ggt gga atg ttt tat cag tat tgc ttt cat gat     912
Gln Gln Asn Gly Asn Gly Gly Met Phe Tyr Gln Tyr Cys Phe His Asp
    290                 295                 300 gat tat tag                                                         921
Asp Tyr
305

<210> SEQ ID NO 2
<211> LENGTH: 306
<212> TYPE: PRT
<213> ORGANISM: Arabidopsis thaliana

<400> SEQUENCE: 2

Met Glu Glu Ala Ile Met Arg Leu Glu Gly Ala Glu His Arg Glu Thr
1               5                   10                  15

Asn Ile His Ser Leu Lys Arg Lys Pro Ser Arg Thr Ser Ser Thr Ala
            20                  25                  30

Pro Gly Ser Pro Gly Gly Val Thr Thr Ala Lys Ala Ala Ser Gly Ala
        35                  40                  45

Gly Ala Ser Gly Val Ser Thr Ile Arg Tyr Arg Gly Val Arg Arg Arg
    50                  55                  60

Pro Trp Gly Arg Tyr Ala Ala Glu Ile Arg Asp Pro Leu Ser Lys Glu
65                  70                  75                  80

Arg Arg Trp Leu Gly Thr Phe Asp Thr Ala Glu Glu Ala Ala Cys Ala
                85                  90                  95

Tyr Asp Cys Ala Ala Arg Ala Met Arg Gly Leu Lys Ala Arg Thr Asn
            100                 105                 110

Phe Val Tyr Pro Met Pro Ser Leu Asp Ser Tyr His His Arg Ile Phe
        115                 120                 125

Ser Ser Pro Pro Met Asn Met Phe Leu Leu Arg Asp Val Leu Asn Ser
    130                 135                 140

Gln Ser Leu Ser Pro Leu Thr Thr Phe Ala Tyr Pro Pro Cys Asn Leu
145                 150                 155                 160

Ser Asn Val Asn Asp Val Val His Glu Ser Phe Thr Asn Val Asn Asp
                165                 170                 175

Val Cys Glu Asp Leu Ser Pro Lys Ala Lys Arg Ser Ser Thr Ile Glu
            180                 185                 190

Asn Glu Ser Leu Ile Ser Asn Ile Phe Glu Pro Glu Pro Ala Ser Ser
        195                 200                 205
```

-continued

```
Gly Leu Leu Gln Glu Ile Val Gln Gly Phe Leu Pro Lys Pro Ile Ser
    210                 215                 220

Gln His Ala Ser Ile Pro Pro Lys Ser Asn Gln Gln Ser Val Gly Val
225                 230                 235                 240

Phe Pro Thr Met Pro Glu Ser Gly Phe Gln Thr Asp Val Arg Leu Ala
                245                 250                 255

Asp Phe His Val Glu Gly Asn Gly Phe Gly Val Lys Tyr His Gly
                260                 265                 270

Glu Leu Gly Trp Ala Asp His Glu Asn Gly Phe Asp Ser Ala Lys Met
            275                 280                 285

Gln Gln Asn Gly Asn Gly Gly Met Phe Tyr Gln Tyr Cys Phe His Asp
290                 295                 300

Asp Tyr
305
```

<210> SEQ ID NO 3
<211> LENGTH: 1265
<212> TYPE: DNA
<213> ORGANISM: Arabidopsis thaliana
<220> FEATURE:
<221> NAME/KEY: CDS
<222> LOCATION: (76)..(1059)

<400> SEQUENCE: 3

```
ggaaactatc aaccaccaaa atctttcaca ttacaccttc cttttgtcct caaaccaaaa      60
ccctagaaac caaaa atg gaa aaa gcc ttg aga aac ttc acc gaa tct acc     111
                Met Glu Lys Ala Leu Arg Asn Phe Thr Glu Ser Thr
                  1               5                  10 cac tca cca gac cct aat cct ctc aca aaa ttc ttc act gaa cct aca     159
His Ser Pro Asp Pro Asn Pro Leu Thr Lys Phe Phe Thr Glu Pro Thr
        15                  20                  25 gcc tca cct gtt agc cgc aac cgc aaa ctg tct tca aaa gat acc act     207
Ala Ser Pro Val Ser Arg Asn Arg Lys Leu Ser Ser Lys Asp Thr Thr
    30                  35                  40 gta acc atc gcc gga gct ggc agc agc acg acg agg tac cgc ggc gta     255
Val Thr Ile Ala Gly Ala Gly Ser Ser Thr Thr Arg Tyr Arg Gly Val
45                  50                  55                  60 cgc cgg agg ccg tgg gga cga tac gcg gcg gag ata cgt gac cca atg     303
Arg Arg Arg Pro Trp Gly Arg Tyr Ala Ala Glu Ile Arg Asp Pro Met
                65                  70                  75 tcg aag gag aga cgt tgg ctc gga aca ttt gac acg gcg gaa caa gcc     351
Ser Lys Glu Arg Arg Trp Leu Gly Thr Phe Asp Thr Ala Glu Gln Ala
            80                  85                  90 gct tgt gct tac gac tct gcg gct cgt gcc ttt cgt gga gca aag gct     399
Ala Cys Ala Tyr Asp Ser Ala Ala Arg Ala Phe Arg Gly Ala Lys Ala
        95                  100                 105 cgt act aat ttt act tat ccg aca gct gtc att atg cct gaa cca agg     447
Arg Thr Asn Phe Thr Tyr Pro Thr Ala Val Ile Met Pro Glu Pro Arg
    110                 115                 120 ttt tct ttt tcc aac aag aaa tct tcg ccg tct gct cgt tgt cct ctt     495
Phe Ser Phe Ser Asn Lys Lys Ser Ser Pro Ser Ala Arg Cys Pro Leu
125                 130                 135                 140 cct tct cta ccg tta gat tcc tct acc caa aac ttt tac ggt gca ccg     543
Pro Ser Leu Pro Leu Asp Ser Ser Thr Gln Asn Phe Tyr Gly Ala Pro
                145                 150                 155 gca gcg cag agg atc tat aat aca cag tct atc ttc tta cgc gac gcc     591
Ala Ala Gln Arg Ile Tyr Asn Thr Gln Ser Ile Phe Leu Arg Asp Ala
            160                 165                 170 tcg tgt tcc tct cgt aaa acg act ccc tat aat aac tct ttc aac ggc     639
```

```
Ser Cys Ser Ser Arg Lys Thr Thr Pro Tyr Asn Asn Ser Phe Asn Gly
        175                 180                 185 tca tca tct tct tac tca gca tcg aaa acg gca tgc gtt tct tat tcc    687
Ser Ser Ser Ser Tyr Ser Ala Ser Lys Thr Ala Cys Val Ser Tyr Ser
    190                 195                 200 gaa aac gaa aac aac gag tcg ttt ttc ccg gaa gaa tct tct gat act    735
Glu Asn Glu Asn Asn Glu Ser Phe Phe Pro Glu Glu Ser Ser Asp Thr
205                 210                 215                 220 ggt cta tta caa gag gtc gtt caa gag ttc ttg aag aaa aat cgc ggc    783
Gly Leu Leu Gln Glu Val Val Gln Glu Phe Leu Lys Lys Asn Arg Gly
                225                 230                 235 gtt cct cct tct cca cca aca cca ccg gtg act agc cat cat gac        831
Val Pro Pro Ser Pro Pro Thr Pro Pro Val Thr Ser His His Asp
            240                 245                 250 aac tct ggt tat ttc tct gct ctc act ata tac tct gaa aat atg gtt    879
Asn Ser Gly Tyr Phe Ser Ala Leu Thr Ile Tyr Ser Glu Asn Met Val
            255                 260                 265 caa gag act aag gag act ttg tcg tcg aaa cta gat cgc tac ggg aat    927
Gln Glu Thr Lys Glu Thr Leu Ser Ser Lys Leu Asp Arg Tyr Gly Asn
        270                 275                 280 ttt caa gct aat gac gac ggc gta aga gcc gtc gca gac ggt ggt tta    975
Phe Gln Ala Asn Asp Asp Gly Val Arg Ala Val Ala Asp Gly Gly Leu
285                 290                 295                 300 tct ttg gga tca aac gag tgg ggg tat caa gaa atg ttg atg tac gga    1023
Ser Leu Gly Ser Asn Glu Trp Gly Tyr Gln Glu Met Leu Met Tyr Gly
                305                 310                 315 act cag tta ggc tgt act tgc cga aga tcg tgg gga tagctagata         1069
Thr Gln Leu Gly Cys Thr Cys Arg Arg Ser Trp Gly
            320                 325 ttcatcatga ttatgttttg agttttggta ctatcgactt agtttaaagt tgctaccttt  1129
cccaatgttg gatattaact aaattatgtt ttaagttgaa tttgctaata ggatttcata  1189
attataatca agtttataat atattttagt agctaattaa agtttatatc cacgtattct  1249
gaaaaaaaaa aaaaaa                                                  1265

<210> SEQ ID NO 4
<211> LENGTH: 328
<212> TYPE: PRT
<213> ORGANISM: Arabidopsis thaliana

<400> SEQUENCE: 4

Met Glu Lys Ala Leu Arg Asn Phe Thr Glu Ser Thr His Ser Pro Asp
1               5                   10                  15

Pro Asn Pro Leu Thr Lys Phe Phe Thr Glu Pro Thr Ala Ser Pro Val
            20                  25                  30

Ser Arg Asn Arg Lys Leu Ser Ser Lys Asp Thr Thr Val Thr Ile Ala
        35                  40                  45

Gly Ala Gly Ser Ser Thr Thr Arg Tyr Arg Gly Val Arg Arg Arg Pro
    50                  55                  60

Trp Gly Arg Tyr Ala Ala Glu Ile Arg Asp Pro Met Ser Lys Glu Arg
65                  70                  75                  80

Arg Trp Leu Gly Thr Phe Asp Thr Ala Glu Gln Ala Ala Cys Ala Tyr
                85                  90                  95

Asp Ser Ala Ala Arg Ala Phe Arg Gly Ala Lys Ala Arg Thr Asn Phe
            100                 105                 110

Thr Tyr Pro Thr Ala Val Ile Met Pro Glu Pro Arg Phe Ser Phe Ser
        115                 120                 125
```

-continued

```
Asn Lys Lys Ser Ser Pro Ser Ala Arg Cys Pro Leu Pro Ser Leu Pro
    130                 135                 140

Leu Asp Ser Ser Thr Gln Asn Phe Tyr Gly Ala Pro Ala Ala Gln Arg
145                 150                 155                 160

Ile Tyr Asn Thr Gln Ser Ile Phe Leu Arg Asp Ala Ser Cys Ser Ser
                165                 170                 175

Arg Lys Thr Thr Pro Tyr Asn Asn Ser Phe Asn Gly Ser Ser Ser Ser
            180                 185                 190

Tyr Ser Ala Ser Lys Thr Ala Cys Val Ser Tyr Ser Glu Asn Glu Asn
        195                 200                 205

Asn Glu Ser Phe Phe Pro Glu Glu Ser Ser Asp Thr Gly Leu Leu Gln
    210                 215                 220

Glu Val Val Gln Glu Phe Leu Lys Lys Asn Arg Gly Val Pro Pro Ser
225                 230                 235                 240

Pro Pro Thr Pro Pro Val Thr Ser His His Asp Asn Ser Gly Tyr
                245                 250                 255

Phe Ser Ala Leu Thr Ile Tyr Ser Glu Asn Met Val Gln Glu Thr Lys
                260                 265                 270

Glu Thr Leu Ser Ser Lys Leu Asp Arg Tyr Gly Asn Phe Gln Ala Asn
            275                 280                 285

Asp Asp Gly Val Arg Ala Val Ala Asp Gly Leu Ser Leu Gly Ser
        290                 295                 300

Asn Glu Trp Gly Tyr Gln Glu Met Leu Met Tyr Gly Thr Gln Leu Gly
305                 310                 315                 320

Cys Thr Cys Arg Arg Ser Trp Gly
                325
```

<210> SEQ ID NO 5
<211> LENGTH: 987
<212> TYPE: DNA
<213> ORGANISM: Arabidopsis thaliana
<220> FEATURE:
<221> NAME/KEY: CDS
<222> LOCATION: (1)..(984)

<400> SEQUENCE: 5

```
atg gaa aaa gcc ttg aga aac ttc acc gaa tct acc cac tca cca gac     48
Met Glu Lys Ala Leu Arg Asn Phe Thr Glu Ser Thr His Ser Pro Asp
1               5                   10                  15 cct aat cct ctc aca aaa ttc ttc act gaa cct aca gcc tca cct gtt     96
Pro Asn Pro Leu Thr Lys Phe Phe Thr Glu Pro Thr Ala Ser Pro Val
                20                  25                  30 agc cgc aac cgc aaa ctg tct tca aaa gat acc act gta acc atc gcc    144
Ser Arg Asn Arg Lys Leu Ser Ser Lys Asp Thr Thr Val Thr Ile Ala
            35                  40                  45 gga gct ggc agc agc acg acg agg tac cgc ggc gta cgc cgg agg ccg    192
Gly Ala Gly Ser Ser Thr Thr Arg Tyr Arg Gly Val Arg Arg Arg Pro
        50                  55                  60 tgg gga cga tac gcg gcg gag ata cgt gac cca atg tcg aag gag aga    240
Trp Gly Arg Tyr Ala Ala Glu Ile Arg Asp Pro Met Ser Lys Glu Arg
65                  70                  75                  80 cgt tgg ctc gga aca ttt gac acg gcg gaa caa gcc gct tgt gct tac    288
Arg Trp Leu Gly Thr Phe Asp Thr Ala Glu Gln Ala Ala Cys Ala Tyr
                85                  90                  95 gac tct gcg gct cgt gcc ttt cgt gga gca aag gct cgt act aat ttt    336
Asp Ser Ala Ala Arg Ala Phe Arg Gly Ala Lys Ala Arg Thr Asn Phe
            100                 105                 110 act tat ccg aca gct gtc att atg cct gaa cca agg ttt tct ttt tcc    384
```

```
Thr Tyr Pro Thr Ala Val Ile Met Pro Glu Pro Arg Phe Ser Phe Ser
        115                 120                 125 aac aag aaa tct tcg ccg tct gct cgt tgt cct ctt cct tct cta ccg      432
Asn Lys Lys Ser Ser Pro Ser Ala Arg Cys Pro Leu Pro Ser Leu Pro
        130                 135                 140 tta gat tcc tct acc caa aac ttt tac ggt gca ccg gca gcg cag agg      480
Leu Asp Ser Ser Thr Gln Asn Phe Tyr Gly Ala Pro Ala Ala Gln Arg
145                 150                 155                 160 atc tat aat aca cag tct atc ttc tta cgc gac gcc tcg tgt tcc tct      528
Ile Tyr Asn Thr Gln Ser Ile Phe Leu Arg Asp Ala Ser Cys Ser Ser
                165                 170                 175 cgt aaa acg act ccg tat aat aac tct ttc aac ggc tca tca tct tct      576
Arg Lys Thr Thr Pro Tyr Asn Asn Ser Phe Asn Gly Ser Ser Ser Ser
            180                 185                 190 tac tca gca tcg aaa acg gca tgc gtt tct tat tcc gaa aac gaa aac      624
Tyr Ser Ala Ser Lys Thr Ala Cys Val Ser Tyr Ser Glu Asn Glu Asn
        195                 200                 205 aac gag tcg ttt ttc ccg gaa gaa tct tct gat act ggt cta tta caa      672
Asn Glu Ser Phe Phe Pro Glu Glu Ser Ser Asp Thr Gly Leu Leu Gln
    210                 215                 220 gag gtc gtt caa gag ttc ttg aag aaa aat cgc ggc gtt cct cct tct      720
Glu Val Val Gln Glu Phe Leu Lys Lys Asn Arg Gly Val Pro Pro Ser
225                 230                 235                 240 cca cca aca cca ccg ccg gtg act agc cat cat gac aac tct ggt tat      768
Pro Pro Thr Pro Pro Pro Val Thr Ser His His Asp Asn Ser Gly Tyr
                245                 250                 255 ttc tct aat ctc act ata tac tct gaa aat atg gtt caa gag act aag      816
Phe Ser Asn Leu Thr Ile Tyr Ser Glu Asn Met Val Gln Glu Thr Lys
            260                 265                 270 gag act ttg tcg tcg aaa cta gat cgc tac ggg aat ttt caa gct aat      864
Glu Thr Leu Ser Ser Lys Leu Asp Arg Tyr Gly Asn Phe Gln Ala Asn
        275                 280                 285 gac gac ggc gta aga gcc gtc gca gac ggt ggt tta tcg ttg gga tca      912
Asp Asp Gly Val Arg Ala Val Ala Asp Gly Gly Leu Ser Leu Gly Ser
    290                 295                 300 aac gag tgg ggg tat caa gaa atg ttg atg tac gga act cag tta ggc      960
Asn Glu Trp Gly Tyr Gln Glu Met Leu Met Tyr Gly Thr Gln Leu Gly
305                 310                 315                 320 tgt act tgc cga aga tcg tgg gga tag                                  987
Cys Thr Cys Arg Arg Ser Trp Gly
                325

<210> SEQ ID NO 6
<211> LENGTH: 328
<212> TYPE: PRT
<213> ORGANISM: Arabidopsis thaliana

<400> SEQUENCE: 6

Met Glu Lys Ala Leu Arg Asn Phe Thr Glu Ser Thr His Ser Pro Asp
1               5                   10                  15

Pro Asn Pro Leu Thr Lys Phe Phe Thr Glu Pro Thr Ala Ser Pro Val
            20                  25                  30

Ser Arg Asn Arg Lys Leu Ser Ser Lys Asp Thr Thr Val Thr Ile Ala
        35                  40                  45

Gly Ala Gly Ser Ser Thr Thr Arg Tyr Arg Gly Val Arg Arg Arg Pro
    50                  55                  60

Trp Gly Arg Tyr Ala Ala Glu Ile Arg Asp Pro Met Ser Lys Glu Arg
65                  70                  75                  80

Arg Trp Leu Gly Thr Phe Asp Thr Ala Glu Gln Ala Ala Cys Ala Tyr
```

```
                        85                  90                  95
Asp Ser Ala Ala Arg Ala Phe Arg Gly Ala Lys Ala Arg Thr Asn Phe
                100                 105                 110
Thr Tyr Pro Thr Ala Val Ile Met Pro Glu Pro Arg Phe Ser Phe Ser
        115                 120                 125
Asn Lys Lys Ser Ser Pro Ser Ala Arg Cys Pro Leu Pro Ser Leu Pro
        130                 135                 140
Leu Asp Ser Ser Thr Gln Asn Phe Tyr Gly Ala Pro Ala Ala Gln Arg
145                 150                 155                 160
Ile Tyr Asn Thr Gln Ser Ile Phe Leu Arg Asp Ala Ser Cys Ser Ser
                165                 170                 175
Arg Lys Thr Thr Pro Tyr Asn Asn Ser Phe Asn Gly Ser Ser Ser Ser
            180                 185                 190
Tyr Ser Ala Ser Lys Thr Ala Cys Val Ser Tyr Ser Glu Asn Glu Asn
        195                 200                 205
Asn Glu Ser Phe Phe Pro Glu Glu Ser Ser Asp Thr Gly Leu Leu Gln
    210                 215                 220
Glu Val Val Gln Glu Phe Leu Lys Lys Asn Arg Gly Val Pro Pro Ser
225                 230                 235                 240
Pro Pro Thr Pro Pro Val Thr Ser His His Asp Asn Ser Gly Tyr
            245                 250                 255
Phe Ser Asn Leu Thr Ile Tyr Ser Glu Asn Met Val Gln Glu Thr Lys
            260                 265                 270
Glu Thr Leu Ser Ser Lys Leu Asp Arg Tyr Gly Asn Phe Gln Ala Asn
        275                 280                 285
Asp Asp Gly Val Arg Ala Val Ala Asp Gly Gly Leu Ser Leu Gly Ser
    290                 295                 300
Asn Glu Trp Gly Tyr Gln Glu Met Leu Met Tyr Gly Thr Gln Leu Gly
305                 310                 315                 320
Cys Thr Cys Arg Arg Ser Trp Gly
                325

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
taggcgcgcc atggaagaag                                              20

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
gcggccgcat ttctttacaa c                                            21
```